United States Patent [19]

Hargrave et al.

[11] Patent Number: 5,550,117
[45] Date of Patent: Aug. 27, 1996

[54] DIPYRIDO[3,2-B:2',3'-E][1,4]DIAQZEPINES AND THEIR USE IN THE TREATMENT OF HIV INFECTION

[75] Inventors: Karl D. Hargrave, Brookfield; Ernest Cullen; John R. Proudfoot, both of Newtown; Karl G. Grozinger, Ridgefield; Kollol Pal, New Milford; Julian Adams, Ridgefield, all of Conn.

[73] Assignee: Boehringer Ingelheim Pharmaceuticals, Inc., Ridgefield, Conn.

[21] Appl. No.: 366,130

[22] Filed: Dec. 29, 1994

Related U.S. Application Data

[63] Continuation of Ser. No. 239,628, May 9, 1994, abandoned, which is a continuation of Ser. No. 95,780, Jul. 21, 1993, abandoned, which is a continuation of Ser. No. 964,241, Oct. 21, 1992, abandoned, which is a continuation of Ser. No. 837,715, Feb. 19, 1992, abandoned, which is a continuation of Ser. No. 652,147, Feb. 7, 1991, abandoned.

[51] Int. Cl.$^6$ ............... A61K 31/55; C07D 487/14
[52] U.S. Cl. ............... 514/81; 514/220; 540/542; 540/557
[58] Field of Search ............... 540/542, 557; 514/81, 220

[56] References Cited

U.S. PATENT DOCUMENTS

| | | | |
|---|---|---|---|
| 5,087,625 | 2/1992 | Hargrave et al. | 514/220 |
| 5,366,972 | 11/1994 | Hargrave et al. | 514/220 |

OTHER PUBLICATIONS

J. Benditt and J. Cohen, *Science*, vol. 260, May 28, 1993, pp. 1253–1255.

Sandstrom et al., Review Article in *Drugs*, 34, pp. 373–390 (1987).

Yarchoan et al, *Aids: Modern Concepts and Therapeutic Challanges*, Marcel Dekker Inc., pp. 335–360 (1987).

Hahn et al, "Nucleotide Dimers as Anti–Human Immuno–deficiency Virus Agents," in Nucleotide Analogues are. Antiviral Agents, Martin ed., Amer. Chem. Soc., pp. 156–159 (1989).

March, *Advanced Organic Chem.*, 3rd ed (1985), pp. 527–529.

*Primary Examiner*—Philip I. Datlow
*Attorney, Agent, or Firm*—Robert P. Raymond; Alan R. Stempel; Mary-Ellen M. Devlin

[57] ABSTRACT

Disclosed are novel dipyrido[3,2-b:2',3'-e][1,4]diazepines and their use in the treatment of HIV-1 infection. An exemplary species is 6-chloro-11-cyclopropyl-4-methyl-11H-dipyrido[3,2-b:2',3'-e][1,4]diazepine, which has the following chemical structure:

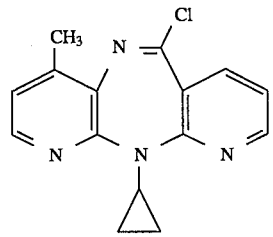

6 Claims, No Drawings

DIPYRIDO[3,2-B:2',3'-E][1,4]DIAQZEPINES AND THEIR USE IN THE TREATMENT OF HIV INFECTION

This is a continuation of application Ser. No. 239,628, filed May 9, 1994 now abandoned, which is a continuation of application Ser. No. 095,780, filed Jul. 21, 1993, now abandoned, which is a continuation of application Ser. No. 964,241, filed Oct. 21, 1992, now abandoned, which is a continuation of application Ser. No. 837,715, filed Feb. 19, 1992, now abandoned, which is a continuation of application Ser. No. 652,147, filed Feb. 7, 1991, now abandoned.

FIELD OF THE INVENTION

The invention relates to novel dipyrido[3,2-b:2',3'-e][1,4] diazepines and pharmaceutically acceptable acid addition salts thereof, methods for preparing these compounds, the use of these compounds in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required vital proteins. The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Next, acting as a fibonuclease, RT frees the DNA just produced from the original viral RNA and then destroys the original RNA. Finally, acting as a DNA-dependent DNA polynerase, RT makes a second, complementary DNA strand, using the first DNA strand as a template. The two strands form double-stranded DNA, which is integrated into the host cell's genome by another enzyme called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

DESCRIPTION OF THE INVENTION

In one of its composition of matter aspects, the invention comprises dipyrido[3,2-b:2',3'-e][1,4]diazepines of the formula I

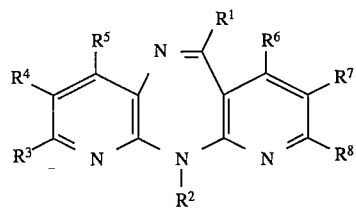

wherein,

R$^1$ is cyano, chloro, bromo, imidazolyl, phosphetanyl, phospholanyl, or phosphorinanyl, or a group of the formula —OR$^9$, —SR$^9$, —SOR$^9$, —SO$_2$R$^9$, —NH$_2$, —NHR$^9$, —NR$^9$R$^{10}$, —PR$^9$R$^{10}$, —P(OR$^9$)(OR$^{10}$)— P(O)(OR$^9$)(OR$^{10}$), —PO$_3$H$_2$, —P(NR$^9$R$^{10}$)(NR$^9$R$^{10}$), or —P(O)(NR$^9$R$^{10}$), wherein R$^9$ and R$^{10}$ are each independently alkyl of 1 to 4 carbon atoms, which may optionally be substituted by a cyano or alkoxycarbonyl group of 2 to 4 carbon atoms, cyclopropyl or cyclobutyl, or the group —NR$^9$R$^{10}$ may be pyrrolidine, piperidine, or morpholine;

R$^2$ is hydrogen, alkyl of 1 to 6 carbon atoms, fluoroalkyl of 1 to 6 carbon atoms and 1 to 3 fluorine atoms, cycloalkyl of 3 to 6 carbon atoms, oxetanyl, thietanyl, tetrahydrofuranyl or tetrahydrothienyl, alkenyl or alkynyl of 2 to 6 carbon atoms, alkyloxyalkyl or alkylthioalkyl of 2 to 5 carbon atoms, alkanoyl of 2 to 5 carbon atoms, cyano, hydroxyalkyl of 2 to 6 carbon atoms, aryl or arylmethyl (wherein the aryl moiety is thiazolyl, oxazolyl, or isoxazolyl, which is unsubstituted, or is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 5 carbon atoms;

one of R$^3$, R$^4$ and R$^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy-alkyl or alkylthioalkyl of 2 to 5 carbon atoms, alkyloxycarbonylalkyl wherein the alkyl moieties each contain 1 to 2 carbon atoms, hydroxyl, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or di-alkylaminocarbonyl wherein each alkyl moiety contains 1 to 3 carbon atoms, aminoalkyl of 1 to 4 carbon atoms, mono- or di-alkylaminoalkyl wherein each alkyl moiety contains 1 to 3 carbon atoms, aryl or arylmethyl (wherein the aryl moiety is phenyl, thienyl or furanyl, which is either unsubstituted or substituted by alkyl or alkyloxy of 1 to 3 carbon atoms, hydroxyl or halogen), a group of the formula —NR$^{11}$R$^{12}$, halogen, cyano, nitro, azido or carboxyl, with the other two substituents being hydrogen, methyl or chloro; or, two of R$^3$, R$^4$ and R$^5$ are independently alkyl or hydroxyalkyl of 1 to 2 carbon atoms, trihalomethyl, alkyloxy or alkylthio of 1 to 2 carbon atoms, halogen or a group of the formula —NR$^{11}$R$^{12}$, with the remaining substituent being hydrogen or methyl; or, R$^3$, R$^4$ and R$^5$ are each hydrogen;

one of R$^6$, R$^7$ and R$^8$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 4 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkoxycarbonyl wherein the alkyl moiety contains 1 to 3 carbon atoms, aminoalkyl of 1 to 4 carbon atoms, mono- or di-alkylamino-alkyl wherein each alkyl moiety contains 1 to 2 carbon atoms, a group of the formula $-NR^{13}R^{14}$, halogen, cyano, nitro, azido or carboxyl, with the other two substituents being hydrogen; or, two of $R^6$, $R^7$ and $R^8$ are independently alkyl of 1 to 2 carbon atoms, trihalomethyl, alkyloxy or alkylthio of 1 to 2 carbon atoms, halogen or a group of the formula $-NR^{13}R^{14}$, with the remaining substituent being hydrogen; or, $R^6$, $R^7$ and $R^8$ are each hydrogen; and, $R^{11}$, $R^{12}$, $R^{13}$ and $R^{14}$ are each independently hydrogen, alkyl of 1 to 4 carbon atoms, alkenylmethyl or alkynylmethyl of 2 to 4 carbon atoms, aryl or arylmethyl (wherein the aryl moiety is phenyl, thienyl or furanyl, which is either unsubstituted or substituted by methyl, methoxy or halogen), mono- or dihydroxyalkylmethyl of 2 to 4 carbon atoms, alkyloxy of 1 to 3 carbon atoms, hydroxy, alkyloxyethyl or alkylthioethyl of 3 to 4 carbon atoms, aminoalkylmethyl of 1 to 4 carbon atoms, mono- or dialkylaminoalkylmethyl wherein each alkyl moiety contains 1 or 2 carbon atoms, or alkanoyl of 1 to 4 carbon atoms; or, $R^{11}$ and $R^{12}$, and $R^{13}$ and $R^{14}$, together with the nitrogen atoms between them, respectively and independently form azetidin-1-yl or a 5, 6 or 7-membered ring which is either saturated or unsaturated, which optionally contains up to one additional heteroatom which may be selected from O, S or N, or which optionally contains in place of a carbon atom a group of the formula $=NR^{15}$ wherein $R^{15}$ is hydrogen or alkyl or 1 to 2 carbon atoms, and which ring is optionally and independently substituted with hydroxymethyl, aminomethyl, 1 to 4 methyl groups and 1 to 2 hydroxy groups.

A subgeneric aspect of the invention comprises compounds of formula I, wherein, $R^1$ is cyano, chloro, bromo, imidazolyl, or a group of the formula $-OR^9$, $-SR^9$, $-SOR^9$, $-SO_2R^{10}$, $-NH_2$, $-NHR^9$, or $-NR^9R^{10}$, wherein $R^9$ and $R^{10}$ are each independently alkyl of 1 to 4 carbon atoms, which may optionally be substituted by a cyano or alkoxycarbonyl group of 2 to 4 carbon atoms, cyclopropyl or cyclobutyl, or the group $-NR^9R^{10}$ may be pyrrolidine, piperidine, or morpholine;

$R^2$ is hydrogen, alkyl of 1 to 5 carbon atoms, fluoroalkyl of 1 to 5 carbon atoms, cycloalkyl of 3 to 5 carbon atoms, oxetanyl, thietanyl, alkenylmethyl or alkynylmethyl of 3 to 5 carbon atoms, alkyloxyalkyl or alkylthioalkyl of 2 to 4 carbon atoms, alkanoyl of 2 to 4 carbon atoms, hydroxyalkyl of 2 to 5 carbon atoms, aryl or arylmethyl (wherein the aryl moiety is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 4 carbon atoms;

one of $R^3$, $R^4$ and $R^5$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 3 carbon atoms, hydroxyalkyloxy of 2 to 3 carbon atoms, alkanoyloxy of 2 to 3 carbon atoms, alkylsulfinyl or alkylsulfonyl of 1 to 3 carbon atoms, alkanoyl of 2 to 4 carbon atoms, alkyloxycarbonyl wherein the alkyl moiety contains 1 to 2 carbon atoms, aminoalkyl of 1 to 3 carbon atoms, mono- or di-alkylaminoalkyl wherein each alkyl moiety contains 1 to 2 carbon atoms, amino, mono- or di-alkylamino wherein each alkyl moiety contains 1 to 4 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, N,N-bis(2-hydroxyethyl)amino, N,N-bis(2-methoxyethyl)amino, or halogen, with the other two substituents being hydrogen, methyl or chloro; or, two of $R^3$, $R^4$ and $R^5$ are independently alkyl of 1 to 2 carbon atoms, alkyloxy or alkylthio of 1 to 2 carbon atoms, amino, mono- or di-alkylamino wherein each alkyl moiety contains 1 to 3 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, N,N-bis(2-hydroxyethyl)amino, N,N-bis(2-methoxyethyl)amino, or halogen, with the remaining substituent being hydrogen, methyl or chloro; or, $R^3$, $R^4$ and $R^5$ are each hydrogen; and, one of $R^6$, $R^7$ and $R^8$ is alkyl of 1 to 2 carbon atoms, vinyl, trifloromethyl, hydroxyalkyl of 1 to 2 carbon atoms, hydroxyl, alkyloxy or alkylthio of 1 to 2 carbon atoms, hydroxyalkyloxy of 2 to 3 carbon atoms, alkanoyloxy of 2 to 3 carbon atoms, amino, mono- or di-alkylamino wherein each alkyl moiety contains 1 to 2 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, N,N-bis(2-hydroxyethyl)amino, N,N-bis(2-methoxyethyl)amino, or halogen, with the other two substituents being hydrogen; or, $R^6$, $R^7$ and $R^8$ are each hydrogen.

A particular subgeneric aspect of the invention comprises compounds of formula I wherein, $R^1$ is cyano, chloro, imidazolyl, or a group of the formula $-OR^9$, $-SR^9$, $-SOR^9$, $-SO_2R^9$, $-NH_2$, $-NHR^9$, or $-NR^9R^{10}$, wherein $R^9$ and $R^{10}$ are each independently alkyl of 1 to 4 carbon atoms, which may optionally be substituted by a cyano or alkoxycarbonyl group of 2 to 4 carbon atoms, cyclopropyl or cyclobutyl, or the group $-NR^9R^{10}$ may be pyrrolidine, piperidine, or morpholine;

$R^2$ is alkyl of 2 to 3 carbon atoms, or cycloalkyl of 3 to 4 carbon atoms;

$R^3$ is hydrogen, methyl, alkyloxy or alkylthio of 1 to 3 carbon atoms, chloro, amino, mono- or di-alkylamino wherein each alkyl moiety contains 1 to 3 carbon atoms, allylamino, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, or N,N-bis(2-hydroxyethyl)amino;

$R^4$ is hydrogen, methyl or chloro;

$R^5$ is hydrogen, methyl, ethyl, chloro, or trifluoromethyl;

$R^6$ and $R^8$ are hydrogen; and $R^7$ is hydrogen or amino.

A more particular subgeneric aspect of the invention comprises compounds of formula I wherein, $R^1$ is cyano, chloro, imidazolyl, or a group of the formula $-OR^9$, $-SR^9$, $-SOR^9$, $-SO_2R^9$, $-NH_2$, $-NHR^9$, or $-NR^9R^{10}$, wherein $R^9$ and $R^{10}$ are each independently alkyl of 1 to 4 carbon atoms, which may optionally be substituted by a cyano or alkoxycarbonyl group of 2 to 4 carbon atoms, cyclopropyl or cyclobutyl, or the group $-NR^9R^{10}$ may be pyrrolidine, piperidine, or morpholine;

$R^2$ is alkyl of 2 to 3 carbon atoms, or cycloalkyl of 3 to 4 carbon atoms;

$R^3$ is hydrogen, methyl, chloro, methoxy, ethoxy, amino, mono- or di-alkylamino wherein each alkyl moiety contains 1 to 2 carbon atoms, allylamino, allylmethylamino, pyrrolin-1-yl, pyrrolidin-1-yl, tetrahydropyridin-1-yl, piperidin-1-yl or morpholin-1-yl;

$R^4$ is hydrogen;

$R^5$ is hydrogen, methyl, ethyl, chloro, or trifluoromethyl;

$R^6$ and $R^8$ are hydrogen; and $R^7$ is hydrogen or amino.

Synthesis Of Compounds Of Formula I And Their Salts

The compounds of Formula I and their salts can be prepared by known methods or obvious modifications thereof. Methods A–J, described below, are illustrative of the methods for preparing the compounds.

Method A (nitrile)

Compounds of the formula I, wherein $R^2$ through $R^8$ are as defined above and $R^1$ is cyano, can be obtained by treating a trifluoromethanesulfonate of formula I, wherein $R^2$ through $R^8$ are as defined above and $R^1$ is trifluoromethanesulfonate, with cyanide ion. Convenient sources of cyanide ion include, for example, tetraethylammonium cyanide, diethylaluminum cyanide, potassium cyanide, or sodium cyanide. The reaction is preferably carried out in an inert solvent, for example, methylene chloride, chloroform, dimethylformamide, dimethylsulfoxide, diethylether, or tetrahydrofuran, at a temperature between 0° C. and the boiling point of the reaction mixture.

Method B (halide)

Compounds of the formula I, wherein $R^2$ through $R^8$ are as defined above and $R^1$ is chloro or bromo, can be obtained by treating a lactam of the formula II,

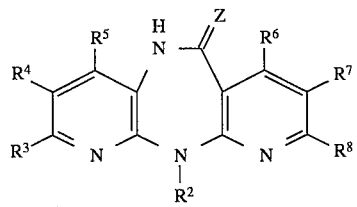
(II)

wherein $R^2$ through $R^8$ are as defined above and Z is oxygen, with a halogenating agent in an inert solvent. Chlorinating agents which may be used include, for example, phosphorus pentachloride, phosphorus oxychloride, and sulfuryl chloride. Brominating agents which may be used include, for example, phosphorus pentabromide or phosphorus oxybromide. The reaction is conveniently carried out at temperatures of between 0° C. and the boiling point of the reaction mixture, preferably at temperatures above ambient temperature, and inert solvents which may be used include, for example, toluene, xylene, dichloroethane, or trichlorobenzene.

Method C (alkoxide)

Compounds of the formula I, wherein $R^1$ is a group of the formula $-OR^9$, and $R^2$ through $R^9$ are as defined above, may be obtained by reacting a compound of the formula I, wherein $R^1$ is cyano and $R^2$ through $R^8$ are as defined above, with an alcohol of formula $R^9OH$. The condensation is conveniently carried out in the presence of a base including, but not limited to, an alkali metal or alkaline earth metal hydroxide, such as lithium hydroxide, barium hydroxide, sodium hydroxide or potassium hydroxide, or an alkali metal alkoxide, such as sodium methoxide or potassium tert-butoxide, and using the alcohol as solvent, at a temperature between −20° C. and +50° C. It is preferable that the alkali metal alkoxide utilized be derived from the alcohol which is used as solvent.

Method D (alkylthio)

Compounds of the formula I, wherein $R^1$ is a group of the formula $-SR^9$, and $R^2$ through $R^9$ are as defined above, may be obtained by converting a compound of the formula II, wherein $R^2$ through $R^8$ are as defined above and Z is sulfur, into the corresponding 5-alkali or alkaline earth metal compound and subsequently reacting the alkali metal compound with a compound of the formula III $$R^9X \qquad (III)$$

wherein $R^9$ has the same meanings as defined above and X is the radical of a reactive ester, a halogen atom, the group $OSO_2R$, wherein R is methyl, ethyl or an aromatic group.

The conversion of a compound of formula II into the corresponding alkali metal or alkaline earth metal compound may be effected by reacting a compound of formula II with an alkali metal or alkaline earth metal hydroxide, such as lithium hydroxide, barium hydroxide, sodium hydroxide or potassium hydroxide, with an alkali metal alkoxide, such as sodium methoxide or potassium tert-butoxide, with an alkali metal amide, such as sodium amide or potassium amide, or with an alkali metal hydride such as sodium hydride or potassium hydride. The reaction is preferably carried out at temperatures between −78° C. and +50° C., and in the presence of a suitable organic solvent. Inert organic solvents, such as dimethylformamide, dimethylsulfoxide, tetrahydrofuran, glycoldimethyl ether, toluene, pyridine, or methylene chloride are preferred. For conversion of the alkali or alkaline earth metal-substituted compound thus obtained into a compound of formula I, the solution or suspension of the alkali or alkaline earth metal compound is reacted directly, i.e. without isolation, with a compound of formula III. Substitution takes place at the sulfur atom in the 6-position of the dipyridodiazepinone, even if $R^2$ in the starting material of formula II is a hydrogen atom, provided that one equivalent of base and one equivalent of a compound of formula III are used.

It will be obvious to those skilled in the art that the presence of nucleophilic substituents in the compounds of formula II may require the use of an intermediate of formula II having substituents which are, other than the 11-position nitrogen, not nucleophilic but which can be derivatized to yield the required group. For example, amino or monoalkylamino substituents at any of $R^3$ through $R^8$ may be obtained by alkylating or acylating an intermediate of formula II having a nitro group at any of $R^3$ through $R^8$, and subsequently reducing the nitro group, and alkylating, if appropriate, to yield the final product.

Method E (sulfoxide)

Compounds of the formula I, wherein $R^1$ is a group of the formula $—SOR^9$, and $R^2$ through $R^9$ are as defined above, may be obtained by oxidizing a compound of the formula I, wherein $R^1$ is a group of the formula $—SR^9$ and $R^2$ through $R^9$ are as defined above. Oxidizing agents which may be used include peroxides such as 30% hydrogen peroxide, peracids such as m-chloroperbenzoic acid or trifluoroperacetic acid, sodium periodate, sodium perborate, or t-butyl hypochlorite. The reaction is carried out in inert solvents such as methylene chloride, dichloroethane, acetic acid, acetone, and toluene at temperatures generally from $-78°$ C. up to the boiling point of the reaction mixture.

Method F (sulfone)

Compounds of the formula I, wherein $R^1$ is a group of the formula $—SO_2R^9$, and $R^2$ through $R^9$ are as defined above, may be obtained by oxidizing a compound of the formula I, wherein $R^1$ is a group of the formula $—SR^9$ or $—SOR^9$, and $R^2$ through $R^9$ are as defined above. Oxidizing agents which may be used include peroxides such as 30% hydrogen peroxide, potassium permanganate, potassium hydrogen persulfate, peracids such as m-chloroperbenzoic acid or trifluoroperacetic acid, sodium periodate, sodium perborate, or t-butyl hypochlorite. The reaction can be carried out in inert solvents such as methylene chloride, dichloroethane, acetic acid, acetone, and toluene at temperatures generally from $-78°$ C. to $25°$ C. Generally, these reactions are performed analogous to those for for the preparation of the corresponding sufoxides, except that an additional equivalent of oxidizing agent is utilized, and the reaction may be carried out at higher temperatures.

Method G (amine)

Compounds of formula I, wherein $R^1$ is a group of the formula $—NHR^9$, $—NR^9R^{10}$, or imidazolyl, and $R^2$ through $R^{10}$ are as defined above, may be obtained by reaction of a compound of formula I, wherein $R^1$ is trifluoromethanesulfonate, with a molar excess of ammonia or an amine of the formula $H_2NR^9$, $HNR^9R^{10}$, or 1-imidazolyl. The condensation is generally carried out in an inert solvent such as methylene chloride, 1,4-dioxane, dimethylformamide, dimethylsulfoxide, tetrahydrofuran, or toluene, at temperatures between $-20°$ C. up to the boiling point of the solvent.

Method H (phosphorous compounds)

Compounds of formula I, wherein $R^1$ is a group of the formula $—PR^9R^{10}$, $—P(OR^9)(OR^{10})$, $—P(O)(OR^9)(OR^{10})$, $—P(NR^9R^{10})(NR^9R^{10})$, $—P(O)(NR^9R^{10})(NR^9R^{10})$, P-phosphetanyl, P-phospholanyl, or P-phosphorinanyl, and $R^2$ through $R^9$ are as defined above, may be obtained by transmetallation of a compound of formula I, wherein $R^1$ is halogen with a bully alkyllithium reagent such as t-butyllithium. The reaction is generally carried out in inert solvents such as tetrahydrofuran, diethyl ether, 1,4-dioxane, and glycoldimethyl ether. The lithio derivative thus formed is then reacted with an appropriate halophosphorous compound of the formula $XPR^9R^{10}$, $XP(OR^9)(OR^{10})$, $XP(O)(OR^9)(OR^{10})$, $XP(NR^9R^{10})(NR^9R^{10})$, $XP(O)(NR^9R^{10})(NR^9R^{10})$, P-halo-phosphetanyl, P-halo-phospholanyl, or P-halophosphorinanyl, wherein X is halogen. These reactions are generally carried out in a single reaction vessel at temperatures between $-78°$ C. and room temperature.

Method I (phosphonic acids)

Compounds of formula I, wherein $R^1$ is a group of the formula $—PO_3H_2$ and $R^2$ through $R^8$ are as defined above, may be obtained by hydrolysis of a compound of formula I, wherein $R^1$ is a group of formula $—P(OR^9)(OR^{10})$, wherein $R^2$ through $R^{10}$ are as defined above. The hydrolysis is generally carried out in an aqueous solution containing an alkaline earth metal hydroxide, such as lithium hydroxide, barium hydroxide, sodium hydroxide or potassium hydroxide, optionally in the presence of an inert organic solvent such as methanol or ethanol, at temperatures between $0°$ C. and the boiling point of the reaction mixture.

Starting Materials for Methods A through I

The preparation of compounds of formula I wherein $R^1$ is trifluoromethanesulfonate and $R^2$ through $R^{10}$ are as defined above, and compounds of formula II wherein $R^2$ through $R^{10}$ are as defined above, can be obtained by procedures described in U.S. Pat. No. 5,366,972.

Those skilled in the art will realize that it will at times be more convenient to make certain compounds of formula I by derivatization of other compounds of formula I, rather than by making them directly, using one of the above-described Methods A–J. Such derivatizations will employ known reaction techniques. As non-limiting examples, a nitro group can be reduced to yield an amine; a methoxy group can convened to hydroxy by standard demethylation procedures and hydroxy can, in appropriate settings, be in turn replaced with amine via the trifluoromethanesulfonyloxy derivative; an amine can be acylated to yield an alkanoylamine or can be alkylated to yield the mono- or dialkylamine; a halogen can be replaced, in appropriate settings, by an amine; and a protecting group can be removed.

Formation Of Salts And Other Derivatives

Compounds of formula I may, if desired, be convened into their non-toxic, pharmaceutically acceptable addition salts by conventional methods; for example, by dissolving a compound of formula I in a suitable solvent and treating the solution with one or more molar equivalents of the desired acid or base, as appropriate. The invention also comprises such salts.

Examples of inorganic and organic acids which may form nontoxic, pharmaceutically acceptable acid addition salts with a compound of the formula I are the following: hydrochloric acid, hydrobromic acid, sulfuric acid, phosphoric acid, nitric acid, methanesulfonic acid, tartaric acid, fumaric acid, acetic acid, and the like. Examples of inorganic and organic bases which may form nontoxic, pharmaceutically acceptable basic addition salts with a compound of the formula I are the following: Sodium hydroxide, potassium hydroxide, magnesium hydroxide, ammonia, tromethamine, and the like. Compounds of formula I may form addition salts with one molar equivalent of the acid or base, as appropriate.

Biological Properties

The above described compounds of formula I, and their salts, possess inhibitory activity against HIV-1 reverse transcriptase. When administered in suitable dosage forms, they are useful in the prevention or treatment of AIDS, ARC and related disorders associated with HIV-1 infection. Another aspect of the invention, therefore, is a method for preventing or treating HIV-1 infection which comprises administering to a human being, exposed to or infected by HIV-1, a prophylactically or therapeutically effective amount of a novel compound of Formula I, as described above.

The compounds of formula I may be administered in single or divided doses by the oral, parenteral or topical routes. A suitable oral dosage for a compound of formula I would be in the range of about 0.5 mg to 1 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenyl-ethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAY

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials:

a) Preparation of the enzyme

Reverse transcriptase enzyme from the LAV strain of Human Immunodeficiency Virus (HIV-1) (1) was isolated from the bacterial strain JM109 (3) expressing the DNA clone pBRTprt1+(2) which is under the control of the lac promotor in the expression vector plBI21 (4). An overnight culture grown in 2XYT medium (37° C., 225 rpm) (5) supplemented with 100 μg/ml ampicillin for positive selection is inoculated at a 1:40 dilution into M9 medium supplemented with 10 μg/ml thiamine, 0.5% casamino acids, and 50 μg/ml ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/ml) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2X concentrated stock reaction mixture

| Stock Reagent | 2X Mix Concentration |
| --- | --- |
| 1M Tris pH 7.8 | 100 mM |
| 1M Dithiothrietol | 4.8 mM |
| 1M KCl | 42 mM |
| 1M MgCl$_2$ | 3.6 mM |
| [poly r(C)/oligo d(G)](5:1) | 2 μg/ml |
| $^3$H-dGTP (81 μM) | 6 μM |
| human serum albumin | 0.25 mg/ml |
| pH 7.8 | |

Assay Procedure:

The 2X concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microliter plates (10 μl/well; 3 wells/compound). The HIV-1 RT enzyme is thawed, diluted in 50 mM Tris pH 7.8 so that fifteen μl of diluted enzyme contain 0.001 Unit (one unit is that amount of enzyme to transform 1 micromole of substrate per minute at 25° C.), and fifteen μl are dispensed per well. Twenty μl of 0.12–0.5M EDTA are added to the first three wells of the microtiter plate. EDTA chelates the $Mg^{++}$ present and prevents reverse transcription. This group serves as background polymerization which is subtracted from all other groups. Twenty-five ul of the 2X reaction mixture are added to all wells and the assay is allowed to incubate at room temperature for 60 minutes. The assay is terminated by precipitating the DNA in each well with 50 μl of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mls of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value} \times 100}{CPM \text{ Mean Control Value}}$$

REFERENCES

1. Benn, S., et al., *Science*, 230:949, 1985
2. Farmerie, W. G. et. al., *Science*, 236:305, 1987
3. Yanisch-Perron, C., Viera, J., and Messing, J., *Gene*, 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982
6. Spira, T., et. al. *J. Clinical Microbiology*, 25:97, 1987.

In order to confirm that compounds which are active in the RT Assay also have the ability to inhibit HIV replication in a living system, compounds according to the invention were also tested in the human T-Cell Culture Assay described below. The results of this testing appear in Table I.

HUMAN T-CELL CULTURE ASSAY

Assay Theory:

Formation of syncytia is a feature of in vitro cultures of CD4+ T-cells infected with HIV-1. In this assay, T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method:

The target cells, designated c8166, are a subclone of human lymphoma cells of T-cell origin and are established at an initial density of $5\times10^4$ per 100 ul in RPMI 1640 (+10% fetal bovine serum) culture medium in 96 well flat bottom plates. A selected amount of test compound, dissolved in DMSO, is included. After 24 hours, 50–100 $TCID_{50}$'s (the dose that results in induced effect in 50% of test cultures) of the HTLV-IIIB strain of HIV-1 (2) are inoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

REFERENCES (1) M. Somasundaran and H. L. Robinson, *Science*, 242:1554 (1988).
(2) G. M. Shaw, R. H. Hahn, S. K. Arya, J. E. Groopman, R. C. Gallo and F. Wong-Staal, *Science*, 226:1165 (1984)

In-order to assess the specificity of the enzyme inhibitory activity of the compounds provided by the invention, a few were tested, using known per se assay methods, for their ability to inhibit Calf Thymus-derived DNA α-polymerase. None of the compounds so tested was observed to possess any inhibitory activity against this enzymes. These results indicate that the enzyme inhibitory activity of the compounds provided by the invention is directed rather specifically against HIV-1 RT.

In order to roughly assess the cytotoxicity of the compounds provided by the invention, several such compounds were tested in the MTT Cellular Cytotoxicity Assay described below. The results of this testing are reported in Table I, below. Compounds having a relatively high $EC_{50}$ are preferred.

MTT ASSAY FOR CELLULAR CYTOTOXICITY

Assay Theory:

The MTT [3-(4,5-dimethylthiazol-2-yl)-2,5 diphenyl tetrazolium bromide) assay is based on cleavage of tetrazolium bromide by metabolically active cells, resulting in a highly quantitative blue color. This assay has been previously described (1) but has been optimized for the purposes of the testing reported herein.

Assay Method:

The c8166 cell line (2), an established human lymphoma suspension cell line grown in RPMI 1640 supplemented with 10% fetal bovine serum, is used as the target cell line in the assay. Cells (100 μl) are plated in microtest plate wells at a concentration of $10^5$ cells per ml in the presence of varying concentrations of inhibitor. The cells are incubated at 37° C. in a humidified $CO_2$ incubator. Five days later, 20 μl of MTT (5 mg/ml in RPMI 1640, sonicated, 0.2 micron filtered, and stored at 4° C.) is added to each well. After 4 hours additional incubation at 37° C. 60 μl of Triton-X is added to each well and thoroughly mixed to aid the solubilization of the crystals. Absolute ethanol (5 μl) is added to each well and the resulting mixture is incubated for 30 minutes at 60° C. and immediately read on a plate reader (Dynatech) at a wavelength of 570 nm. Data from this assay are used to generate a nonlinear regression analysis which yields an $EC_{50}$.

REFERENCES

1. Mosmann, Tim, *J. Immunol. Methods*, 65:55, 1983.
2. Salahuddin, S. Z., Markham, P. D., Wong-Staal, F., Franchini, G., Kalyanaraman, V. S., Gallo, R. C., *Virol.*, 129:51, 1983.

TABLE I

| Compound of Example No. | RT Assay % inhibition @ 10 μg/ml | T-Cell Assay % inhibition @ 3 μg/ml | Cytotoxicity Assay ($CC_{50}$, μg/ml) |
|---|---|---|---|
| 1 | 99 | >90 | >5 |

TABLE I-continued

| Compound of Example No. | RT Assay % inhibition @ 10 µg/ml | T-Cell Assay % inhibition @ 3 µg/ml | Cytotoxicity Assay (CC$_{50}$, µg/ml) |
|---|---|---|---|
| 2 | 98 | >50 | 28 |
| 3 | 99 | >50 | NT |
| 4 | 100 | NT | NT |
| 5 | 98 | NT | NT |
| 6 | 98 | NT | NT |
| 7 | 92 | NT | NT |
| 8 | 99 | NT | NT |
| 9 | 97 | NT | NT |
| 10 | 91 | NT | NT |
| 11 | 97 | NT | NT |
| 12 | 96 | NT | NT |
| 13 | 99 | NT | NT |
| 14 | 100 | NT | NT |
| 15 | 99 | NT | NT |

NT = not tested

EXAMPLES

The following examples further illustrate the present invention and will enable others skilled in the art to understand it more completely. It should be understood, however, that the invention is not limited to the particular examples given below.

Example 1

6-Chloro-11-cyclopropyl-4-methyl-11H-dipyrido[3,2-b:2',3'-e][1,4]diazepine

A mixture of 1.00 g (3.76 mmole) of 11-cyclopropyl-5,11-dihydro-4-methyl-6H-dipyrido[3,2 -b:2',3'-e][1,4]diazepin-6-one, 0.79 g (3.79 mmole) of phosphorus pentachloride and 25 mL of toluene was refluxed for 30 min., then cooled and poured onto crushed ice. The mixture was extracted with three 100 mL portions of methylene chloride, and the extract was dried (magnesium sulfate), filtered and concentrated in vacuo. The residue was chromatographed over silica gel (eluted with 25% ethyl acetate/hexane) to give 0.52 g of a solid, which was recrystallized from heptane to give 0.40 g (1.39 mmol) of the title compound, m.p. 196°–198° C.

Example 2

6-Cyano-11-cyclopropyl-4-methyl-11H-dipyrido[3,2-b:2',3'-e][1,4]diazepine a.) 11-Cyclopropyl-4-methyl-6-trifluoromethanesulfonyloxy-11H-dipyrido[3,2-b:2',3'-e][1,4]-diazepine Trifluoromethanesulfonic anhydride (5.02 g, 17.8 mmole) was added dropwise to a cooled mixture of 3.00 g (11.3 mmole) of 11-cyclopropyl-5,11-dihydro-4-methyl-6H-dipyrido[3,2-b: 2',3'-e][1,4]diazepin-6-one, 2.32 g (18.0 mmole) of diisopropylethylamine, and 45 mL of methylene chloride. After the addition was complete, the ice bath was removed and the mixture was stirred for one hour. Ethyl acetate (500 mL) was added and the resulting solution was washed with three 100 mL portions of water. The organic solution was dried (magnesium sulfate), filtered, and concentrated in vacuo. The residue was chromatographed over silica gel (eluted with 50% ethyl acetate/hexane) to provide 3.18 g (8.0 mmole) of the title compound as a yellow oil, suitable for the next reaction.

b.) 6-Cyano-11-cyclopropyl-4-methyl-11H-dipyrido[3,2-b:2',3'-e][1,4]diazepine

A solution of 2.56 g (6.42 mmole) of the trifluoromethanesulfonate prepared above and 1.14 g (7.28 mmole) of tetraethylammonium cyanide in 100 mL of methylene chloride was stirred overnight at room temperature. Solvent was then removed in vacuo and the residue was extracted twice with 100 mL portions of refluxing heptane. The solution was concentrated in vacuo and the residue was chromatographed over silica (eluted with 50% ethyl acetate-hexane). The product was recrystallized from heptane to yield 0.42 g (1.53 mmole) of the title compound. m.p. 192°–193° C.

Example 3

6-Cyano-2,4-dimethyl-11-ethyl-11H-dipyrido[3,2-b:2',3'-e][1,4]diazepine

Trifluoromethanesulfonic anhydride (0.24 mL, 14 mmol) was added to a solution of 0.314 g (1.2 mmol) 5,11-dihydro-2,4-dimethyl-11-ethyl-6H-dipyrido[3,2-b:2',3'-e][1,4]diazepine-6-one in 15 mL of methylene chloride containing 0.25 mL (14 mmol) of diisopropylethylamine. The resulting mixture was refluxed under Ar for 3 hr. Ethyl acetate (~200 mL) was then added and the solution was washed three times with water and four times with brine. After drying (magnesium sulfate), the solution was concentrated in vacuo and the residue dried under high vacuum for 2 hr. The residue was dissolved in 20 mL of methylene chloride, and 0.23 g (14 mol) of tetraethylammonium cyanide was added. After stirring the resulting solution overnight at room temperature, the reaction mixture was concentrated in vacuo. The residue was dissolved in 100 mL of ethyl acetate, and the solution washed with water and brine, and then dried (magnesium sulfate). The solution was concentrated in vacuo and the residue was chromatographed over silica (eluted with 5% ethyl acetate/hexane). The resulting solid was crystallized from heptane to provide 33 mg of the title compound as red crystals, m.p. 154°–155° C.

Example 4

11-Cyclopropyl-4-methyl-6-methylthio-11H-dipyrido[3,2-b:2',3'-e][1,4]diazepine

To a warm (40° C.) solution of 1.0 g (3.54 mmol) of 11-cyclopropyl-5,11-dihydro-4-methyl- 6H-dipyrido[3,2-b:2',3'-e][1,4]diazepin-6-thione in 25 mL of dry dimethylformamide under argon was added 200 mg (4.43 mmol) of a 60% sodium hydride on mineral oil dispersion. The suspension was heated at 60° for 30 min., cooled to 40° C., and 0.3 mL (4.43 mmol) of iodomethane was added in one portion. After stirring the mixture for 1 hr at room temperature, ethanol was added dropwise until bubbling ceased. The mixture was then poured over 200 mL of water, and the product was extracted with 2×200 mL of ethyl ether. The combined organics were washed with 300 mL of water, dried (Na$_2$SO$_4$), and concentrated. The resulting reddish solid was flash chromatographed over silica gel (eluted with 83% methylene chloride/ethyl acetate) to give a yellow solid. Recrystallization from ethyl ether/petroleum ether gave 350 mg of the title compound, m.p. 173°–177° C.

Example 5

11-Cyclopropyl-6-[S-(ethoxy-2-oxoethyl)]-4-methyl-11H-dipyrido[3,2-b:2',3'-e][1,4]diazepine To a solution of 1.0 g (3.54 mmol) of 11-cyclopropyl-5,11-dihydro-4-methyl-6H-dipyrido[3,2 -b:2;3'-e][1,4]diazepin-6-thione in 25 mL of anhydrous dimethylformamide was added 0.2 g (5.00 mmol) of sodium hydride (60% dispersion in mineral oil) at 40° C. under argon. The mixture was heated at 60° C. for 1 hr, cooled to 40° C., and 0.5 mL (4.43 mmol) of ethyl bromoacetate was added at once. The solution was then stirred an additional 1 hr at 40° C., and methanol was added dropwise until bubbling ceased. The mixture was added to 200 mL of water, and the aqueous layer was partitioned with diethyl ether (2×200 ml). The combined organic layers were washed with water (300 mL), and dried ($Na_2SO_4$). The solution was concentrated to give a red oil which was chromatographed over flash silica gel (eluted with 80% methylene chloride/ethyl acetate) to give 0.60 g (46% of theory) of the title compound as an orange resin.

Example 6

6-Amino-11-cyclopropyl-4-methyl-11H-dipyrido[3,2-b:2',3'-e][1,4]diazepine

To a solution of 11-cyclopropyl-4-methyl-6-trifluoromethanesulfonyloxy-11H-dipyrido[3,2-b:2',3'-e][1,4]diazepine (0.22 g, 0.55 mmol) in 1,4-dioxane (3 mL) was added 30% ammonium hydroxide (3 mL). The mixture was heated at 100° C. for 15 min. After cooling to room temperature the mixture was diluted with ethyl acetate, washed with water, dried (magnesium sulfate), filtered and concentrated in vacuo. The residue was chromatographed over silica gel (eluted with 1:1:1 ethyl acetate/hexane/methylene chloride→50% ethyl acetate/hexane) to give the title compound (0.045 g, 0.17 mmol, 30%) which crystallized from ethyl acetate/hexane, m.p. 242°–244° C.

Example 7

11-Ethyl-6-(n-propylamino)-11H-dipyrido[3,2-b:2',3'-e][1,4]diazepine a.) 6-Chloro-11-ethyl-11H-dipyrido[3,2-b:2',3'-e][1,4]diazepine The title compound, prepared from 11-ethyl-11H-dipyrido[3,2-b:2',3'-e][1,4]diazepine in a manner analogous to that described in Example 1, was used directly in the next reaction without chromatographic purification.

b.) 11-Ethyl-6-(n-propylamino)-11H-dipyrido[3,2-b:2',3'-e][1,4]diazepine

A mixture of 6-chloro-11-ethyl-11H-dipyrido[3,2-b:2',3'-e][1,4]diazepine (0.7 g, n-propylamine (0.8 g), and toluene (25 mL) was heated at reflux for ten days. At two day intervals during the ten day period, additional 1.6 g portions of n-propylamine was added to the refluxing mixture. The mixture was then concentrated in vacuo and the residue chromatographed over silica gel (eluted with 20% ethyl acetate/hexane) to give 0.15 g of the title compound, m.p. 114°–116° C.

Example 8

2,4-Dimethyl-11-ethyl-6-methylthio-11H-dipyrido[3,2-b:2',3'-e][1,4]diazepine

To a solution of 5,11-dihydro-2,4-dimethyl-11-ethyl-6H-dipyrido[3,2-b:2',3'-e][1,4]diazepin-6-thione (0.2 g, 0.7 mmol) in dimethylformamide (10 mL) was added NaH (50% in mineral oil, 0.04 g, 0.8 mmol). The mixture was stirred under argon at 40° C. for 1 hr. After cooling to 30° C. methyl iodide (0.12 g, 0.8 mmol) was added, and the mix was stirred for 1 hr. The reaction was quenched with water, and the mixture was concentrated in vacuo. The residue was treated with ethyl acetate, washed, dried, and concentrated. Chromatography over silica gel (eluted with 20% EtOAc/Hex) gave 0.2 g of the title compound, m.p. 130°–132° C.

Example 9

11-Cyclopropyl-6-(1-imidazolyl)-4-methyl-11H-dipyrido[3,2-b:2',3'-e][1,4]diazepine To a solution of 11-cyclopropyl-4-methyl-6-trifluoromethanesulfonyloxy-11H-dipyrido[3,2-b:2',3'-e][1,4]diazepine (0.12 g, 0.3 mmol) in dioxan (1 mL) was added imidazole (0.06 g, 0.88 mmol). The mixture was heated at 100° C. for 10 min. After cooling to room temperature, the reaction mixture was diluted with ethyl adetate, washed with water, dried over sodium sulfate, filtered and concentrated. The residue was fractionated by preparative layer chromatography (silica gel, eluted with 67% ethyl acetate/hexane) to give the title compound (0.04 g, 0.12 mmol, 42%) which crystallized from di-isopropyl ether, m.p. 198°–200° C.

Example 10

2,4-Dimethyl-11-ethyl-6-pyrrolidino-11H-dipyrido[3,2-b:2',3'-e][1,4]diazepine

11-Cyclopropy-4-methyl-6-trifluoromethanesulfonyloxy-11H-dipyrido[3,2-b:2',3'-e][1,4]diazepine (0.30 g, 0.75 mmol) was dissolved in pyrrolidine (1 mL) and stirred at room temperature for 4 days. The reaction mixture was then diluted with ethyl acetate, washed with water, dried and concentrated. The residue was chromatographed over silica gel (eluted with 15% ethyl acetate/hexane) to give the title compound which crystallized from ethyl acetate/hexane (0.17 g, 0.53 mmol, 70% ), m.p. 138°–140° C.

Example 11

2,4-Dimethyl-6-dimethylamino-11-ethyl-11H-dipyrido[3,2-b:2',3'-e][1,4]diazepine

A mixture of 2,4-dimethyl-11-ethyl-6-trifluoromethanesulfonyloxy-11H-dipyrido[3,2-b:2',3'-e][1,4]diazepine (0.3 g, 0.75 mmole) and dimethylamine (excess, used as solvent) were placed in a sealed pressure tube and left at room temperature for 3 days. The reaction mixture was diluted with ethyl acetate, washed with water, dried, filtered and concentrated. The 260 mg of product thus obtained was recrystallized from ethyl acetate/hexane to give the title compound, m.p. 150°–152° C.

Example 12

2,4-Dimethyl-11-ethyl-6-methylamino-11H-dipyrido[3,2-b:2',3'-e][1,4]diazepine

Methylamine (3 mL) was added to a solution of 2,4-dimethyl-11-ethyl-6-trifluoromethane-sulfonyloxy-11H-dipyrido[3,2-b:2',3'-e][1,4]diazepine (0.16 g, 0.4 mmole) in methylene chloride (0.5 mL). The mixture was sealed in a pressure bottle and stirred at room temperature for 4 days. The mixture was diluted with ethyl acetate, washed with water, dried, filtered and concentrated in vacuo to give crude product. This was purified by chromatography over silica gel (eluted 10% ethyl acetate/methylene chloride) and recrystallized from ethyl acetate/hexane to give 0.016 g of the title compound, m.p. 128°–130° C.

Example 13

11-Cyclopropyl-4-methyl-6-methylsulfinyl-11H-dipyrido[3,2-b:2',3'-e][1,4]diazepine A solution of 11-cyclopropyl-4-methyl-6-methylthio-11H-dipyrido[3,2-b:2',3'-e][1,4]diazepine (0.8 g, 0.0027 mol) in methylene chloride (10 mL) was cooled in an ice water bath. To the resulting clear yellow solution was added m-chloroperbenzoic acid (0.55 g, 0.0027 mol) in one portion and the reaction mixture was stirred at 0° C. for 30 min. A cloudy yellow solution was obtained which was quenched by the addition of Ca(OH)$_2$ (1 g, 0.0135 mol). The reaction mixture was stirred at room temperature for 15 min., filtered through a pad of Celite, and concentrated to obtain a yellow oil. Trituration with ether afforded 0.7 g of the title compound, m.p. 188°–190° C.

Example 14

11-Cyclopropyl-4-methyl-6-methylsulfonyl-dipyrido[3,2-b:2',3'-e][1,4]diazepine To a solution of 11-cyclopropyl-4-methyl-6-methylthio-11H-dipyrido[3,2-b:2',3'-e][1,4]diazepine (0.67 g, 0.0026 mol) in methylene chloride (10 mL) was added m-chloroperbenzoic acid (0.92 g, 0.0045 mol). After stirring the yellow solution at room temperature for 30 min., the resulting cloudy yellow mixture treated with Ca(OH)$_2$ (2.0 g, 0.027 mol) and the reaction stirred for an additional 15 minutes. The mixture was filtered through a pad of Celite, concentrated to a yellow oil, and triturated with ether to afford 0.51 g (68 %) of the title compound as a yellow solid, m.p. 172°–173° C.

Example 15

11-Cyclopropyl-6-methoxy-4-methyl-11H-dipyrido[3,2-b:2',3'-e][1,4]diazepine

A solution of 2N sodium hydroxide (6 mL, 1.2 mmol) was added in three portions over two hr to a solution of 6-cyano-11-cyclopropyl-4-methyl-11H-dipyrido[3,2-b:2',3'-e][1,4]diazepine (0.30 g, 1.1 mmol) in methanol (50 mL) at room temperature. The mixture was stirred overnight, and then concentrated in vacuo. The residue was dissolved in ethyl acetate (150 mL) and washed succesively with water and brine. After drying (MgSO$_4$), the solution was concentrated and crystallized from acetonitrile to give 0.20 g (65%) of the title compound. A second recrystallization from methanol provided pure product, m.p. 191°–192° C.

EXAMPLE A

| Capsules or Tablets | | | |
| --- | --- | --- | --- |
| A-1 Ingredients | Quantity | A-2 Ingredients | Quantity |
| Compound of Ex. 2 | 250 mg | Compound of Ex. 2 | 50 mg |
| Starch | 160 mg | Dicalcium Phosphate | 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 2 is blended into a powder mixture with the premixed excipient materials as identified above with the exception of the lubricant. The lubricant is then blended in and the resulting blend compressed into tablets or filled into hard gelatin capsules.

EXAMPLE B

| Parenteral Solutions | |
| --- | --- |
| Ingredients | Quantity |
| Compound of Example 2 | 500 mg |
| Tartaric acid | 1.5 g |
| Benzyl Alcohol | 0.1% by weight |
| Water for injection q.s. to 100 mL | |

The excipient materials are mixed with the water and thereafter the compound of Example 2 is added. Mixing is continued until the solution is clear. The pH of this solution is adjusted to 3.0 and is then filtered into the appropriate vials or ampoules and sterilized by autoclaving.

EXAMPLE C

| Nasal Solutions | |
| --- | --- |
| Ingredients | Quantity |
| Compound of Example 2 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 ml |

The excipient materials are mixed with the water and thereafter the compound of Example 2 is added and mixing is continued until the solution is clear. The pH of this solution is adjusted to 4.0 and is then filtered into the appropriate vials or ampoules.

We claim:
1. A compound of the formula I

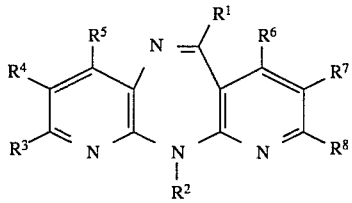

wherein,

R$^1$ is cyano, chloro, bromo, imidazolyl, phosphetanyl, phospholanyl, or phosphorinanyl, or a group of the formula —OR$^9$, —SR$^9$, —SOR$^9$, —SO$_2$R$^9$, —NH$_2$, —NHR$^9$, —NR$^9$R$^{10}$, —PR$^9$R$^{10}$, —P(OR$^9$)(OR$^{10}$), —P(O)(OR$^9$)(OR$^{10}$), —PO$_3$H$_2$, —P(NR$^9$R$^{10}$)(NR$^9$R$^{10}$), or —P(O)(NR$^9$R$^{10}$)(NR$^9$R$^{10}$), wherein R$^9$ and R$^{10}$ are each independently alkyl of 1 to 4 carbon atoms, which may optionally be substituted by a cyano or alkoxycarbonyl group of 2 to 4 carbon atoms, cyclopropyl or cyclobutyl, or the group —NR$^9$R$^{10}$ may be pyrrolidine, piperidine, or morpholine;

R$^2$ is hydrogen, alkyl of 1 to 6 carbon atoms, fluoroalkyl of 1 to 6 carbon atoms and 1 to 3 fluorine atoms, cycloalkyl of 3 to 6 carbon atoms, oxetanyl, thietanyl, tetrahydrofuranyl or tetrahydrothienyl, alkenyl or alkynyl of 2 to 6 carbon atoms, alkyloxyalkyl or alkylthioalkyl of 2 to 5 carbon atoms, alkanoyl of 2 to 5 carbon atoms, cyano, hydroxyalkyl of 2 to 6 carbon atoms, aryl or arylmethyl (wherein the aryl moiety is thiazolyl, oxazolyl, or isoxazolyl, which is unsubstituted, or is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 5 carbon atoms;

one of R$^3$, R$^4$ and R$^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy-alkyl or alkylthioalkyl of 2 to 5 carbon atoms, alkyloxycarbonylalkyl wherein the alkyl moieties each contain 1 to 2 carbon atoms, hydroxyl, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or di-alkylaminocarbonyl wherein each alkyl moiety contains 1 to 3 carbon atoms, aminoalkyl of 1 to 4 carbon atoms, mono- or di-alkylaminoalkyl wherein each alkyl moiety contains 1 to 3 carbon atoms, aryl or arylmethyl (wherein the aryl moiety is phenyl, thienyl or furanyl, which is either unsubstituted or substituted by alkyl or alkyloxy of 1 to 3 carbon atoms, hydroxyl or halogen), a group of the formula —NR$^{11}$R$^{12}$, halogen, cyano, nitro, azido or carboxyl, with the other two substituents being hydrogen, methyl or chloro; or, two of R$^3$, R$^4$ and R$^5$ are independently alkyl or hydroxyalkyl of 1 to 2 carbon atoms, trihalomethyl, alkyloxy or alkylthio of 1 to 2 carbon atoms, halogen or a group of the formula —NR$^{11}$R$^{12}$, with the remaining substituent being hydrogen or methyl; or, R$^3$, R$^4$ and R$^5$ are each hydrogen;

one of R$^6$, R$^7$ and R$^8$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 4 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkoxycarbonyl wherein the alkyl moiety contains 1 to 3 carbon atoms, aminoalkyl of 1 to 4 carbon atoms, mono- or di-alkylamino-alkyl wherein each alkyl moiety contains 1 to 2 carbon atoms, a group of the formula —NR$^{13}$R$^{14}$, halogen, cyano, nitro, azido or carboxyl, with the other two substituents being hydrogen; or, two of R$^6$, R$^7$ and R$^8$ are independently alkyl of 1 to 2 carbon atoms, trihalomethyl, alkyloxy or alkylthio of 1 to 2 carbon atoms, halogen or a group of the formula —NR$^{11}$R$^{14}$, with the remaining substituent being hydrogen; or, R$^6$, R$^7$ and R$^8$ are each hydrogen; and, R$^{11}$, R$^{12}$, R$^{13}$ and R$^{14}$ are each independently hydrogen, alkyl of 1 to 4 carbon atoms, alkenylmethyl or alkynylmethyl of 2 to 4 carbon atoms, aryl or arylmethyl (wherein the aryl moiety is phenyl, thienyl or furanyl, which is either unsubstituted or substituted by methyl, methoxy or halogen), mono- or dihydroxyalkylmethyl of 2 to 4 carbon atoms, alkyloxy of 1 to 3 carbon atoms, hydroxy, alkyloxyethyl or alkylthioethyl of 3 to 4 carbon atoms, aminoalkyl-methyl of 1 to 4 carbon atoms, mono- or dialkylaminoalkylmethyl wherein each alkyl moiety contains 1 or 2 carbon atoms, or alkanoyl of 1 to 4 carbon atoms; or, R$^{11}$ and R$^{12}$, and R$^{13}$ and R$^{14}$, together with the nitrogen atoms between them, respectively and independently form azetidin-1-yl or a 5, 6 or 7-membered ring which is either saturated or unsaturated, which optionally contains up to one additional heteroatom which may be selected from O, S or N, or which optionally contains in place of a carbon atom a group of the formula =NR$^{15}$ wherein R$^{15}$ is hydrogen or alkyl or 1 to 2 carbon atoms, and which ring is optionally and independently substituted with hydroxymethyl, aminomethyl, 1 to 4 methyl groups and 1 to 2 hydroxy groups;

or a pharmaceutically acceptable acid addition salt thereof.

2. A compound of formula I, as set forth in claim 1, wherein,

R$^1$ is cyano, chloro, bromo, imidazolyl, or a group of the formula —OR$^9$, —SR$^9$, —SOR$^9$, —SO$_2$R$^{10}$, —NH$_2$, —NHR$^9$, or —NR$^9$R$^{10}$, wherein R$^9$ and R$^{10}$ are each independently alkyl of 1 to 4 carbon atoms, which may optionally be substituted by a cyano or alkoxycarbonyl group of 2 to 4 carbon atoms, cyclopropyl or cyclobutyl, or the group —NR$^9$R$^{10}$ may be pyrrolidine, piperidine, or morpholine;

R$^2$ is hydrogen, alkyl of 1 to 5 carbon atoms, fluoroalkyl of 1 to 5 carbon atoms, cycloalkyl of 3 to 5 carbon atoms, oxetanyl, thietanyl, alkenylmethyl or alkynylmethyl of 3 to 5 carbon atoms, alkyloxyalkyl or alkylthioalkyl of 2 to 4 carbon atoms, alkanoyl of 2 to 4 carbon atoms, hydroxyalkyl of 2 to 5 carbon atoms, aryl or arylmethyl (wherein the aryl moiety is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 4 carbon atoms;

one of R$^3$, R$^4$ and R$^5$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 3 carbon atoms, hydroxyalkyloxy of 2 to 3 carbon atoms, alkanoyloxy of 2 to 3 carbon atoms, alkylsulfinyl or alkylsulfonyl of 1 to 3 carbon atoms, alkanoyl of 2 to 4 carbon atoms, alkyloxycarbonyl wherein the alkyl moiety contains 1 to 2 carbon atoms, aminoalkyl of 1 to 3 carbon atoms, mono- or di-alkylaminoalkyl wherein each alkyl moiety contains 1 to 2 carbon atoms, amino, mono- or di-alkylamino wherein each alkyl moiety contains 1 to 4 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, N,N-bis(2-hydroxyethyl)amino, N,N-bis(2-methoxyethyl)amino, or halogen, with the other two substituents being hydrogen, methyl or chloro; or, two of $R^3$, $R^4$ and $R^5$ are independently alkyl of 1 to 2 carbon atoms, alkyloxy or alkylthio of 1 to 2 carbon atoms, amino, mono- or di-alkylamino wherein each alkyl moiety contains 1 to 3 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyfidin-1-yl, piperidin-1-yl, morpholin-1-yl, (4-methyl)piperazin-1-yl, piperazin-1-yl, N,N-bis(2-hydroxyethyl)-amino, N,N-bis(2-methoxyethyl)amino, or halogen, with the remaining substituent being hydrogen, methyl or chloro; or, $R^3$, $R^4$ and $R^5$ are each hydrogen; and, one of $R^6$, $R^7$ and $R^8$ is alkyl of 1 to 2 carbon atoms, vinyl, trifluoromethyl, hydroxyalkyl of 1 to 2 carbon atoms, hydroxyl, alkyloxy or alkylthio of 1 to 2 carbon atoms, hydroxyalkyloxy of 2 to 3 carbon atoms, alkanoyloxy of 2 to 3 carbon atoms, amino, mono- or di-alkylamino wherein each alkyl moiety contains 1 to 2 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, N,N-bis(2-hydroxyethyl)amino, N,N-bis(2-methoxyethyl)amino, or halogen, with the other two substituents being hydrogen; or, $R^6$, $R^7$ and $R^8$ are each hydrogen;
or a pharmaceutically acceptable acid addition salt thereof.

3. A compound of formula I, as set forth in claim 1, wherein, $R^1$ is cyano, chloro, imidazolyl, or a group of the formula —$OR^9$, —$SR^9$, —$SOR^9$, —$SO_2R^9$, —$NH_2$, —$NHR^9$, or —$NR^9R^{10}$, wherein $R^9$ and $R^{10}$ are each independently alkyl of 1 to 4 carbon atoms, which may optionally be substituted by a cyano or alkoxycarbonyl group of 2 to 4 carbon atoms, cyclopropyl or cyclobutyl, or the group —$NR^9R^{10}$ may be pyrrolidine, piperidine, or morpholine;

$R^2$ is alkyl of 2 to 3 carbon atoms, or cycloalkyl of 3 to 4 carbon atoms;

$R^3$ is hydrogen, methyl, alkyloxy or alkylthio of 1 to 3 carbon atoms, chloro, amino, mono- or di-alkylamino wherein each alkyl moiety contains 1 to 3 carbon atoms, allylamino, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, or N,N-bis(2-hydroxyethyl)amino;

$R^4$ is hydrogen, methyl or chloro;

$R^5$ is hydrogen, methyl, ethyl, chloro, or trifluoromethyl;

$R^6$ and $R^8$ are hydrogen; and $R^7$ is hydrogen or amino;
or a pharmaceutically acceptable acid addition salt thereof.

4. A compound of formula I, as set forth in claim 1, wherein, $R^1$ is cyano, chloro, imidazolyl, or a group of the formula —$OR^9$, —$SR^9$, —$SOR^9$, —$SO_2R^9$, —$NH_2$, —$NHR^9$, or —$NR^9R^{10}$, wherein $R^9$ and $R^{10}$ are each independently alkyl of 1 to 4 carbon atoms, which may optionally be substituted by a cyano or alkoxycarbonyl group of 2 to 4 carbon atoms, cyclopropyl or cyclobutyl, or the group —$NR^9R^{10}$ may be pyrrolidine, piperidine, or morpholine;

$R^2$ is alkyl of 2 to 3 carbon atoms, or cycloalkyl of 3 to 4 carbon atoms;

$R^3$ is hydrogen, methyl, chloro, methoxy, ethoxy, amino, mono- or di-alkylamino wherein each alkyl moiety contains 1 to 2 carbon atoms, allylamino, allylmethylamino, pyrrolin-1-yl, pyrrolidin-1-yl, tetrahydropyridin-1-yl, piperidin-1-yl or morpholin-1-yl;

$R^4$ is hydrogen;

$R^5$ is hydrogen, methyl, ethyl, chloro, or trifluoromethyl;

$R^6$ and $R^8$ are hydrogen; and $R^7$ is hydrogen or amino;
or a pharmaceutically acceptable salt thereof.

5. A method for treating HIV-1 infection which comprises administering, to a human being exposed to or infected by HIV-1, a therapeutically effective amount of a compound of formula I, as set forth in claims 1, 2, 3, or 4, or a pharmaceutically acceptable acid addition salt thereof.

6. A pharmaceutical composition suitable for treating HIV-1 infection which comprises a therapeutically effective amount of a compound of formula I, as set forth in claims 1, 2, 3, or 4, or a pharmaceutically acceptable acid addition salt thereof, and a pharmaceutically acceptable carrier.

* * * * *